United States Patent [19]

Bose et al.

[11] 4,440,682

[45] Apr. 3, 1984

[54] STEREOSPECIFIC SYNTHESIS OF ISOCEPHALOSPORINS AND 2-OXA ISOCEPHALOSPORINS

[75] Inventors: Ajay K. Bose, Mountain Lakes, N.J.; Isabel F. Fernandez, Madrid, Spain; Kanti J. Gala, Harrison, N.J.

[73] Assignee: Laboratorio Farmaceutico Quimico "LaFarquim, S.A.", Madrid, Spain

[21] Appl. No.: 251,128

[22] Filed: Apr. 6, 1981

[51] Int. Cl.³ ............... C07D 205/08; C07D 498/04; C07D 497/04; C07D 403/12

[52] U.S. Cl. ........................... 260/239 A; 260/245.4; 260/330.3; 544/47; 544/105

[58] Field of Search .......... 260/239 AL, 245.4, 330.3, 260/542; 542/410

[56] References Cited

PUBLICATIONS

T. W. Doyle et al., *Can. J. Chem.*, 55: 2873 (1977).
A. K. Bose et al., *Tetrahedron Let.*, 2771 (1979).
A. K. Bose et al., *Synthesis*, 543 (1979).
A. K. Bose et al., *J. Org. Chem.*, 38, 1238 (1973).
Conway et al., *Can. J. Chem.*, 56, 1335 (1978).

*Primary Examiner*—Mark L. Berch

[57] ABSTRACT

A process is described whereby a synthetically produced 4-styryl-cis-3,4-azetidinone is converted to an isocephalosporin or its 2-oxa analog. The process is based upon the condensation of enamine and imine synthons. Novel intermediate azetidinones are also disclosed. Control of the stereochemical course of the process allows economical, high yield preparation of the racemic form of the product or when a single enantiomer of the imine synthon derived from the β-hydroxy-α-amino acid starting material is used, both enantiomers of the product may be prepared and separated without optical resolution.

6 Claims, No Drawings

STEREOSPECIFIC SYNTHESIS OF ISOCEPHALOSPORINS AND 2-OXA ISOCEPHALOSPORINS

BACKGROUND OF THE INVENTION

Although the penicillins and cephalosporins are widely used in medicine, there is continued interest in obtaining new, synthetic β-lactam antibiotics to combat strains of microorganisms that acquire resistance to β-lactam antibiotics currently in use.

A recently developed approach to the total synthesis of β-lactam antibiotics employs as its key step, the reaction of an α-azidoacyl chloride and an imino compound in the presence of a tertiary amine to form the α-azido-β-lactam nucleus. Several 6-epipenicillin, penam and cepham derivatives have been synthesized from the α-azido-β-lactam intermediate. Reduction of the azido group after β-lactam formation and modification of the α-amino-β-lactam nucleus will provide the desired antibiotic.

Isocephalosporins, which have sulfur positioned at the 2 position of the 6 membered ring instead of the 1 position as in cephalosporins, and 0-2-isocephalosporins which are the oxa analogs have also been synthesized via the α-azido-β-lactam technique.

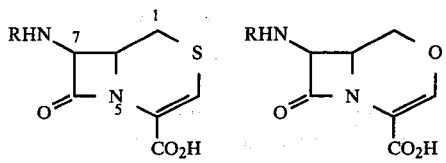

Though not occurring in nature, the isocephalosporins synthesized are reported to have antibiotic activity comparable to that of cephalosporins. [D. B. Bryan et al., *J.Am.Chem.Soc.*, 1977, 99 2352; T. W. Doyle et al., *Can. J. Chem.*, 1977 55, 2873; for a review of the chemistry of the α-azido-β-lactam approach, see B. G. Christensen et al., *Ann. Rev. Med. Chem.*, Chapt. 28, 271 (1976)].

Commercial preparation of any of the β-lactam antibiotics by the α-azido-β-lactam route requires large scale procesing and bulk quantities of reagent ingredients. Unfortunately such quantities and scales create serious drawbacks for the method. For example, the required reagents such as azidoacetic acid and azidoacetyl chloride have been reported to be prone to violent decomposition, especially during such large scale purification techniques as distillation. The reduction of an α-azido-β-lactam to α-amino-β-lactam also requires careful control to ensure a high yield of the desired product. Otherwise, β-lactam cleavage may occur during the reduction and subsequent acylation of the α-azido-β-lactam, [Bose et al., *J. Or. Chem.*, 1973, 38, 1238].

Therefore, development of an alternative synthetic method that is not hazardous and gives high yields without the necessity of precisely controlled conditions is desirable.

Furthermore, the known methods of the preparation of isocephalosporins and analogs involve non-chiral starting material. To obtain biologically active, chiral final products from these known methods, optical resolution of the final product or an intermediate close to the final product is necessary, [See, for example, Conway et al., *Cana. J. Chem.*, 1978, 56, 1335]. Such optical resolution usually leads to the waste of about 50 percent of the β-lactam antibiotic or a close intermediate. Therefore, development of an alternate synthetic method that provides optically active final products without a resolution step is desirable.

OBJECTS OF THE INVENTION

An object of the invention is to provide a process for the high yield preparation of isocephalosporins and 2-oxa-isocephalosporins using economical and safe reactants such as amino acids.

Another object is to provide a process that permits preparation of optically pure enantiomers of the desired isocephalosporins and 2-oxa analogs without the need for optical resolution methods.

A further object is to prepare both enantiomers of the desired isocephalosporins and 2-oxa analogs in the optically active forms from the same optically active β-hydroxy-α-amino acid starting material so as to provide an economical synthesis. For example, a synthesis that uses the readily available L-serine instead of expensive D-serine.

A further object is the correlation of absolute configuration and antibiotic activity of the desired isocephalosporins through use of a chiral synthetic process.

BRIEF DESCRIPTION OF THE INVENTION

In accordance with the objects set forth above, the present invention is comprised of a racemic or enantiomeric cis-3,4-azetidinone of formula VI or an unequal mixture of enantiomers thereof

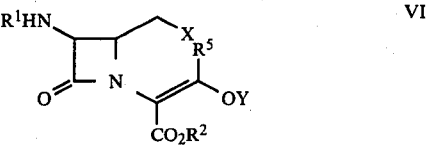

wherein
$R^1$ is an N-acyl side chain of the α-amino-β-lactam antibiotics which is stable to dilute acid and base and to mild oxidation and reduction;
$R^2$ is hydrogen, benzyl, p-nitrobenzyl, phenyl, p-biphenyl or alkyl of 1 to 3 carbon atoms;
$R^5$ is hydrogen, alkyl of 1 to 3 carbons, phenyl, furyl, thienyl, acetoxymethyl or S-(N-methyltetrazol-1-yl)thiamethyl;
X is hydroxy, methanesulfonoxy, p-toluenesulfonoxy, trifluoromethanesulfonoxy, alkylcarbonato of 2 to 4 carbons, benzylcarbonato, chloro, bromo or iodo, and;
Y is methanesulfonyl, p-toluenesulfonyl, trifluoromethanesulfonyl, alkoxycarbonyl of 2 to 4 carbons or benzyloxycarbonyl.

Further, in accordance with these objects, the present invention is comprised of a process for the synthesis of an isocephalosporin of formula I

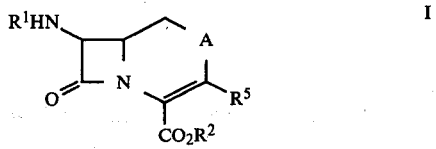

wherein $R^1$ is an N-acyl side chain of the α-amino-β-lactam antibiotics which is stable to dilute acid and base and to mild oxidation and reduction, $R^2$ is hydrogen, benzyl, p-nitrobenzyl, phenyl, p-biphenyl or alkyl of 1 to 3 carbons, $R^5$ is hydrogen, alkyl of 1 to 3 carbons, phenyl, furyl, thienyl, acetoxymethyl or S-(N-methyltetrazol-1-yl)thiamethyl and A is sulfur or oxygen, which comprises:

oxidizing a styryl compound of formula II wherein Y is methanesulfonyl, p-toluenesulfonyl, trifluoromethanesulfonyl, benzyloxycarbonyl or alkoxycarbonyl of 2 to 4 carbons, with a mild, neutral ozidizing agent in aprotic organic solvent;

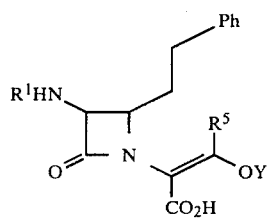

to form an aldehyde of formula III;

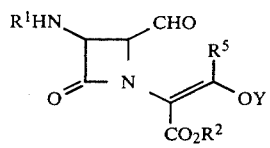

reducing the aldehyde of formula III with a neutral reducing agent in ethereal solvent to form an alcohol of formula IV;

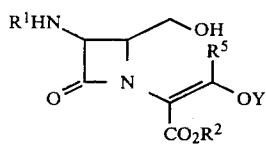

reacting the alcohol of formula IV with a substituting reagent selected from methanesulfonyl chloride or bromide, p-toluenesulfonyl chloride or bromide, trifluoromethanesulfonyl chloride or bromide, alkoxycarbonyl chloride or bromide, benzyloxycarbonyl chloride or bromide, methanesulfonic anhydride, p-toluenesulfonic anhydride or trifluoromethanesulfonic anhydride in aprotic anhydrous organic solvent containing an organic base, or with triphenyl phosphine and carbon tetrachloride or tetrabromide in ethereal solvent or with triphenylphosphite methiodide in ethereal solvent, to form an ester of formula V;

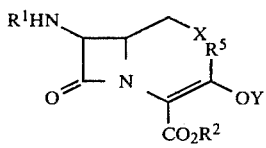

and
condensing the ester of formula V with hydrogen sulfide in ethereal, chlorocarbon or ketonic solvent containing an organic base or with sodium or potassium acetate in polar organic solvent to form an isocephalosporin of formula I.

DETAILED DESCRIPTION OF THE INVENTION

For the purposes of the invention herein described, it will be understood that the hydrogen configuration at the 6 and 7 positions of the isocephalosporin of formula I below is alpha, alpha or beta, beta, or, in other words, the two enantiomers of the cis-6,7 isocephalosporin isomer. Moreover, the monocyclic β-lactams herein described below as intermediates are also understood to have the alpha, alpha or beta, beta hydrogen configuration at positions 3 and 4, i.e., they are cis-β-lactams.

The novel process of the invention involves the synthesis of racemic or enantiomeric 4-carboxy-cis-6,7-isocephalosporins and 2-oxa-isocephalosporins of formula I' or a mixture of enantiomers thereof wherein the 7-amino group is a primary amine optionally substituted with any of the known N-acyl side chains or protecting groups of the α-amino-β-lactam antibiotics, e.g., $R^4$ of formula I'.

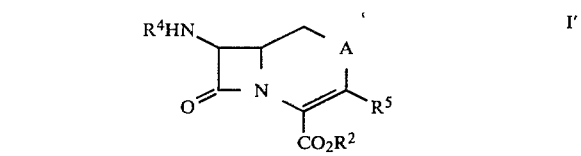

In this process the steric course of synthetic steps is controlled and can lead to the isolation of either enantiomer of isocephalosporin in optical pure form or alternatively can lead to the racemic form or the unequal mixture of enantiomers of the same compounds.

A novel aspect of this steric control is that both enantiomers of isocephalosporin I' may be obtained from a single enantiomer of the starting material amino acid which is preferably the less expensive and more readily available enantiomer.

In accordance with the novel process of the present invention, there is included the selection of such protective groups for the various functional groups in the intermediates that in the preparation of the isocephalosporins and 2-oxa analogs, solids or crystalline materials are obtained at every step thereby making chromatographic purification unnecessary. This feature is especially important for the large scale preparation of the products which will be cheaper if the intermediates do not require purification by chromatography.

More particularly, the invention includes the following processes.

In the first process, a racemic or enantiomeric-cis-3,4-aldehyde of formula III or a mixture of enantiomers thereof

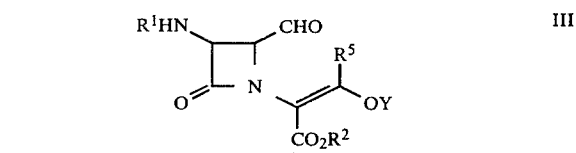

is prepared by oxidizing a racemic or enantiomeric-cis-3,4-styryl compound of formula II or a mixture of enantiomers thereof, with a mild, neutral oxidizing agent in aprotic organic solvent.

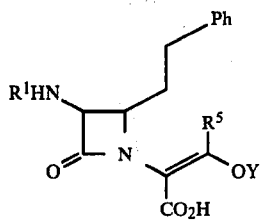

In the second process, a racemic or enantiomeric-cis-3,4-alcohol of formula IV or a mixture of enantiomers thereof is prepared

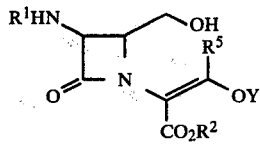

by reducing Aldehyde III with a neutral reducing agent in ethereal solvent.

In the third process, a racemic or enantiomeric cis-3,4-ester of formula V or a mixture of enantiomers thereof is prepared by esterifying the hydroxyl group of Alcohol IV with methanesulfonyl halide, p-toluenesulfonyl halide, trifluoromethanesulfonyl halide, methanesulfonic, p-toluenesulfonic or trifluoromethanesulfonic anhydride, benzyloxycarbonyl halide or alkoxycarbonyl halide of 2 to 4 carbons, or by substituting chloro, bromo or iodo in place of the hydroxyl group by reaction with triphenyl phosphine in carbon tetrachloride or tetrabromide or with triphenyl phosphite methiodide.

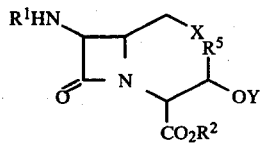

In the fourth process, a racemic or enantiomeric 3-methyl-4-carboxy-cis-6,7-isocephalosporin of formula I above, or a mixture of enantiomers thereof wherein A is S is prepared by condensing Ester V with hydrogen sulfide in inert organic solvent containing a weak organic base. The corresponding isocephalosporin I wherein A is O is prepared by condensing Ester V with sodium or potassium acetate in polar organic solvent.

In formulas I through V, $R^1$ may be any of the known N-acyl side chains or protecting groups of the α-amino-β-lactam antibiotics which are stable to the four processes described above. More particularly, $R^1$ may be $R^3CO$ wherein $R^3$ is (2-thienyl)methyl, (2-thienyl)methoxy, phenyl, benzyl, phenoxy, phenoxymethyl, phenylethyl, phenoxyethyl or the monosubstituted phenyl forms thereof wherein the substituent is halogen, amino, carboxyl, carboxyester of 2 to 7 carbons, carboxamido, N-alkyl carboxamido having 1 to 4 carbons in the alkyl group, alkyl of 1 to 4 carbons or trifluoromethyl. $R^1$ may also be α-alkyl-β-[alkyl or hydrogen]-β-[alkoxycarbonyl or alkylcarbonyl]vinyl having 1 to 3 carbons in each of the alkyl and alkoxy groups. $R^3$ may also be an amino methyl group derived from any of the known α-amino acids such as phenyl glycine, glycine, alanine, serine, cysteine, tyrosine, phenylalanine, 5-amino-5-carboxyvaleric acid and the like. For example, if $R^3$ is $PhCHNH_2$, it would be derived from phenyl glycine, $PhCHNH_2CO_2H$.

In formulas I through V, $R^2$ may be benzyl, p-nitrobenzyl, phenyl, p-biphenyl or alkyl of 1 to 3 carbons and Y may be methanesulfonyl, p-toluenesulfonyl, trifluoromethenesulfonyl, alkoxycarbonyl of 2 to 4 carbons or benzyloxycarbonyl. In these formulas, $R^5$ may be hydrogen, alkyl of 1 to 3 carbons, phenyl, furyl, thienyl, acetoxymethyl or S-(N-methyltetrazol-1-yl)thiamethyl, and X of formula V may be hydroxy, methanesulfonoxy, p-toluenesulfonoxy, trifluoromethanesulfonoxy, alkylcarbonato of 2 to 4 carbons, benzylcarbonato, chloro, bromo or iodo.

$R^4$ of formula I' may be of the known N-acyl side chains or protecting groups of the α-amino-β-lactam antibiotics and A of formulas I and I' may be S or O.

The invention also includes a racemic or enantiomeric cis-3,4-azetidinone of formula VI or a mixture of enantiomers thereof

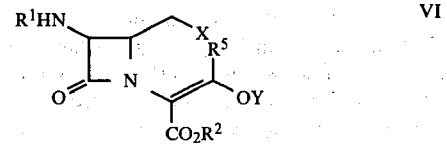

wherein $R^1$, $R^2$, $R^5$, X and Y are defined as above.

Preferred azetidinones of formula VI include those wherein $R^2$ is p-nitrobenzyl, wherein X is hydroxy, wherein X is methanesulfonoxy and Y is methanesulfonyl wherein $R^5$ is methyl or acetoxymethyl and those wherein $R^1$ is $R^3CO$.

Particularly preferred azetidinones of formula VI include those wherein $R^1$ is phenoxyacetyl.

Preferred species of azetidinones of formula VI include the azetidinone wherein $R^1$ is phenoxyacetyl, $R^2$ is p-nitrobenzyl, $R^5$ is methyl, X is hydroxy and Y is methanesulfonyl and the azetidinone wherein $R^1$ is phenoxyacetyl, $R^2$ is p-nitrobenzyl, $R^5$ is methyl, X is methanesulfonoxy and Y is methanesulfonyl.

The intermediate azetidinones and process of the invention lead to the preparation of isocephalosporins of formula I above. The starting material for this synthesis is the styryl compound of formula II above. In applicant's copending applications Ser. No. 969,207, filed Dec. 13, 1978, now abandoned, and Ser. No. 108,669, filed Dec. 31, 1979, now abandoned the synthesis of this styryl compound inter alia is described. The synthesis is also diagrammatically presented in scheme A below.

In this scheme and the corresponding description, the substituents A, $R^1$, $R^2$, $R^3CO$, $R^5$, X and Y of the various formulas are defined as above and the substituents E and Z are as indicated in scheme A. Briefly, the five reactions composing the scheme are as follows.

In reaction 1, the enamine of formula A wherein Z is an activated leaving group such as ethyl carbonato, imidazolyl and the like is condensed with the imine of formula B in ethereal solvent and organic base to produce the α-enamino cis-3,4-β-lactam of formula C.

The two starting materials for this reaction are known. Enamine A is the so-called "Dane salt" or the condensation product of glycine and methyl acetoacetate which has been activated at the glycine carboxylic acid group with a known leaving group such as ethyl carbonate or imidazolyl and the like. Imine B is the schiff base condensation product of cinnamaldehyde and racemic or enantiomeric threonine or threonine substituted by $R^5$ in the $\beta$ position.

When optically active threonine or its $R^5$ derivative is used in the scheme, the enamino-cis-3,4-$\beta$-lactam of formula C and the lactams of formulas D and E exist as diastereomers which can be separated by physical methods such as crystallization or column or high pressure liquid chromatography. Although the separation of diastereomers is most conveniently handled after reaction 1, the separation may also be accomplished after either reactions 2 or 3 of scheme A. This separation permits the economical production of optically pure isocephalosporin and does not require a special "brucine or other alkaloid salt resolution" step for its accomplishment.

In reaction 2, the enamine group of Lactam A is cleaved with p-toluene sulfonic acid or dilute hydrochloric acid in ketonic solvent and the resulting product neutralized with organic base to yield the $\alpha$-amino-cis-3,4-$\beta$-lactam of formula C.

In the reaction 3, the $\alpha$-amine group of Lactam C is condensed with an $R^1$ group donor using reaction conditions well known in the art. For example, when $R^1$ is acyl, the $R^1$ group donor may be the acyl halide and the condensation may be accomplished in aprotic organic solvent containing an organic base. If the desired N-acyl group side chain of $\alpha$-amino-$\beta$-lactam antibiotics would prove unstable to the subsequent reactions of schemes A and B, it is not considered to be within the scope of $R^1$. Instead, such an N-acyl group side chain may be added at the end of the synthetic sequence presented in scheme B. For example, the $\alpha$-amine group of Lactam C may be protected with a protecting group such as benzyloxycarbonyl or t-butoxycarbonyl which may be removed at the end of the synthesis by methods known to those familiar with the art. Any of the known N-acyl group side chains of $\alpha$-amino-$\beta$-lactams, including those which are sensitive to the reaction conditions of schemes A and B, i.e., the group $R^4$, may then be substituted onto the resulting 7-amino group of the isocephalosporin of formula I using techniques known to those familiar with the art.

In reaction 4, mild oxidation of $R^1$-B-Lactam E using no more than 2 equivalents of Jones reagent ($CrO_3/H_2SO_4$) in a 50 fold volume excess of ketonic solvent and esterification of the resulting enone with methanesulfonyl, p-toluenesulfonyl, trifluoromethanesulfonyl, alkoxy carbonyl of 2 to 4 carbons or benzyloxy carbonyl halide in ethereal, chlorocarbon or ketonic solvent and organic base or with methanesulfonic, p-toluenesulfonic or trifluoromethanesulfonic anhydride under similar conditions produces the desired cis-3,4-styryl compound of formula II.

SCHEME A

Preparation of Styryl Compound of Formula II

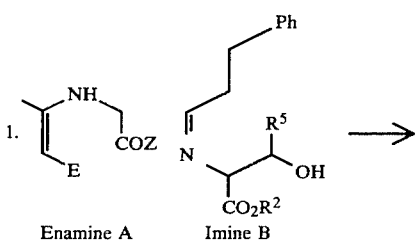

Enamine A   Imine B

-continued

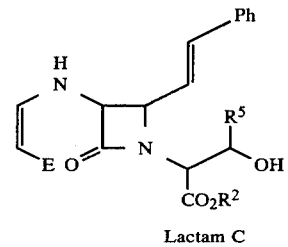

Lactam C $E=CO_2CH_3$, $Z=OCO_2Et$ or the chlorocyanogen reaction product

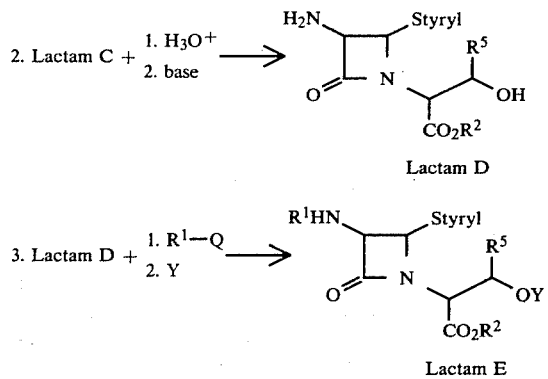

Lactam D

Lactam E

Q is a leaving group such as halogen and the like.

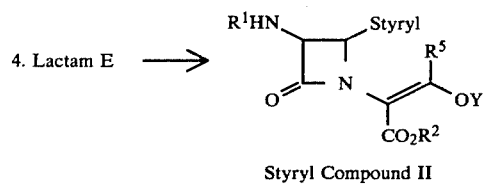

Styryl Compound II

Scheme B presents the synthetic method of the invention whereby the cis-3,4-styryl compound of formula II above is converted through the intermediacy of the cis-3,4-azetidinone of formula VI above to the isocephalosporin of formula I above. In this scheme and the description of it, the substituents A, $R^1$, $R^2$, $R^3CO$, $R^5$, X and Y of the various formulas are defined as above.

Reactions 5 through 8 of Scheme B compose the processes of the invention and may be conducted on racemic or enantiomeric starting materials or enantiomeric mixtures thereof without optical isomerization. Moreover, when Styryl Compound II is prepared from diastereomeric material which has been separated after any reactions 1, 2 or 3 Scheme A, it will be optically pure. This will permit the synthesis of optically pure isocephalosporins and the determination of which isocephalosporin enantiomer demonstrates the highest antibiotic activity.

Reaction 5 is the oxidation of the styryl group of Styryl Compound II to produce the aldehyde of formula III. Ozone is a convenient, mild, neutral oxidizing agent which when passed through a solution of Styryl Compound II in methylene chloride or hexane at $-60°$ C. or below will accomplish this reaction. Ruthenium tetroxide will accomplish the oxidation also.

Reaction 6 is the reduction of Aldehyde III with diborane in ethereal solvent such as ethyl ether or tetrahydrofuran at −60° C. or below to produce the alcohol of formula IV. Diisobutyl aluminum hydride in ethereal or hydrocarbon solvent will also accomplish the reduction. Other similar neutral reducing agents may also be employed with success.

Reaction 7 is reaction of Alcohol IV to produce the ester of formula V. In this reaction, methanesulfonyl, p-toluenesulfonyl, trifluoromethanesulfonyl, alkoxycarbonyl of 2 to 4 carbons or benzyloxycarbonyl halide in ethereal, chlorocarbon or ketonic solvent with organic base such as pyridine, triethylamine, dipropylamine and the like will esterify the alcohol group. Methanesulfonic, p-toluenesulfonic or trifluoromethanesulfonic anhydride in ethereal, chlorocarbon or ketonic solvent with organic base may also be used. In addition in this reaction, triphenyl phosphine and carbon tetrachloride or bromide in ethereal solvent or triphenyl phosphite methiodide in ethereal solvent will cause substitution of chloro, bromo or iodo respectively in place of the alcohol group.

Reaction 8 is the ring closure of Ester V to form the isocephalosporin of formula I. In this reaction when A is S, hydrogen sulfide is added to a solution of Ester V in ethereal, chlorocarbon or ketonic solvent containing an organic base such as pyridine or triethyl amine to affect sulfurization and ring closure. When A is O, Ester V is condensed with sodium or potassium acetate in a polar solvent such as dimethyl formamide to affect ring closure.

If the desired 7-amino substituent of Isocephalosporin I' is incompatible with the reaction sequence presented in schemes A and B, it may be substituted on the isocephalosporin after reaction 8. In this instance, it is convenient to use benzyloxycarbonyl, t-butoxycarbonyl, or other like protecting group as the $R^1$ group present during the synthetic steps. These groups may then be removed after step 8 by methods known to those familiar with the art and the desired 7-amino side chain, $R^4$, is substituted onto the 7-amino group using methods known to those skilled in the art.

Hydrolysis of the $R^2$ group using one equivalent of a dilute base such as sodium bicarbonate in water and alcohol at 0°–5° C. followed by neutralization with dilute acetic acid will produce the isocephalosporin having a carboxylic acid at the 4 position. Hydrogenolysis of the $R^2$ group when it is p-nitrobenzyl using a noble metal catalyst and alcohol will also yield the acid.

SCHEME B

Preparation of Isocephalosporin I

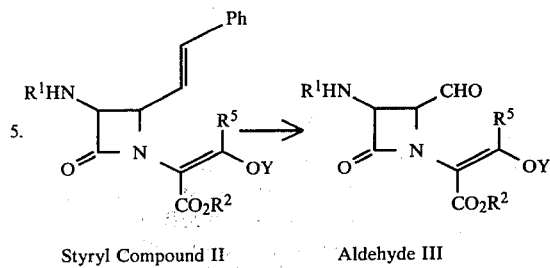

Styryl Compound II       Aldehyde III

6. Aldehyde III →

Alcohol IV

7. Alcohol IV →

Ester V

8. Ester V →

Isocephalosporin

Isocephalosporins are useful as antibiotics in the treatment of bacterial infections. The novel intermediates and processes of the invention provide a safe and economical method for the complete synthesis of a wide range of isocephalosporins. The process is amenable to large scale production and is flexible enough to permit substitution of any of the known amino group side chains of the α-amino-β-lactam antibiotics which can selectively change or enhance the basic antibiotic activity of the β-lactam nucleus.

The following preparations and examples more fully illustrate but do not limit the above-described invention.

EXAMPLE 1

Preparation of Cinnamylidine N-(2-hydroxy-1-p-nitrobenzyloxy propyl)amine (Imine B1)

(a) N-[1-methyl-2-methoxycarbonyl-vinyl]-d-threonine, potassium salt (G)

d-threonine (39.0 g, 328 mmol) and potassium hydroxide (22.02 g, 393 mmol) were dissolved in absolute methanol (700 ml) and the mixture was stirred at room temperature until it became homogeneous. Methyl acetoacetate (41.38 g, 361 mmol) was then added, and the solution stirred overnight. This solution was concentrated to dryness under reduced pressure, and the resulting white solid recrystallized from absolute ethanol to yield 78.2 g of G. This solid was then suspended in methylene chloride (500 ml) and stirred vigorously for 1 hour. The suspended material was then filtered and dried to yield the pure salt G (76.13 g, 91.0%), mp 133°–5°.

Analysis: $C_9H_{14}NO_5K$ requires: C 42.35; H 5.49; N 5.49. Found: C 42.61; H 5.78; N 5.31.

(b) p-Nitrobenzyl d-threonine ester (H)

p-Nitrobenzyl bromide (21.6 g, 100 mmol) and the salt G (25.5 g, 100 mmol) were dissolved in anhydrous dimethylformamide (100 ml), and the solution was stirred at room temperature for 24 hours. The reaction mixture was then diluted with ethyl acetate (300 ml), washed with saturated NaHCO₃, brine, dried (Na₂SO₄), and concentrated in vacuo to yield ester H as a viscous oil (36.5 g). This material, quite pure as determined by TLC, was then dissolved in 1,4-dioxane (80 ml) to which was added p-toluenesulfonic acid monohydrate (19.02 g, 100 mmol). After stirring at room temperature for 20 hours, the product precipitated from solution, was filtered, washed with ether, and dried to yield the p-toluenesulfonate salt (36.04 g, 84.0% from G) as a white, fluffy, solid, mp 142°-3°.

Analysis: $C_{18}H_{22}N_2O_8S$ requires: C 61.36; H 6.25; N 7.95. Found: C 61.55; H 6.48; N 7.81.

By using a similar sequence of reactions p-nitrobenzyl dl-threonine, p-toluenesulfonate was synthesized starting from dl-threonine.

The free threonine ester (H) can be generated by treating the above salts with a base, such as aqueous potassium carbonate solution or triethylamine.

(c) Condensation to form Imine B1

To a solution of p-nitrobenzyl ester of dl-threonine (Ester H) in dry methylene chloride was added an equimolar amount of trans-cinnamaldehyde. The solution was refluxed for 5 min. and then stirred for 1 hr. at room temperature. To remove the water formed in the reaction a quantity of molecular sieve was added and the mixture was stirred for another 1½ hour. The clear solution obtained by filtering was evaporated and the residual yellow oil was triturated with a petroleum ether to obtain the crude Schiff Base, cinnamylidene N-(2-hydroxy-1-p-nitrobenzyloxypropyl)amine which was recrystallized from ethyl acetate, petroleum ether to obtain pure Imine B1 (87%), m.p. 0.98°-99° C.

ir(CHCl₃): 3100, 1750, 1625 cm⁻¹.

NMR(CDCl₃): 1.20 (d.3H, J=7 Hz) 2.80 (s, broad, 1H), 3.85 (d, J=7 Hz, 1H), 4.35, (m, 1H), 525 (3, 2H), 7.00 (d, 2H), 7.2 7.6 (m, 7H) 8.20 (d, 8H, J=3 Hz). CIMS: found M+1=369 (calcd. MW+368).

When the ester H derived from d-threonine was used in the above experiment, an imine B1 was obtained that was noncrystalline but had the same spectral properties as recorded above.

EXAMPLE 2

1-(1'-p-nitrobenzyloxycarbonyl-2'-hydroxy)propyl-3-(1''-methyl-2''-methoxycarbonyl) vinylamino-4-styryl-cis-3,4-azetidin-2-one (Lactam C2)

To a suspension of the potassium salt of (1-methyl-2-methoxycarbonyl) vinylamino acetic acid, Enamine A1 formed according to the procedure given by Bose et al. in *Synthesis*, 1979, 543, (2.96 g. 0.014 mole) 120 ml anhydrous ether was added under anhydrous conditions 3.6 ml (0.028 mole) of triethyl amine at −25° C. Ethyl chloroformate (1.4 ml, 0.014 mole) was then added dropwise and the reaction mixture was stirred for ½ hour. To this mixture was added a solution of the Imine B1 of Example 1 (3.86 g) in 120 ml of dry methylene chloride dropwise over a period of ½ hour at −25° C. and for 1 hour at room temperature and then evaporated to dryness under reduced pressure, then triturated with anhydrous ether, cooled and filtered. The solid residue (which contained the β-lactam and inorganic salts) was extracted with chloroform. This chloroform solution was washed with water, dried and evaporated to dryness. The residual solid was found to be a mixture of two diastereomeric β-lactams by thin layer chromatography. It was estimated from the NMR spectrum that the diastereomers were roughly equal in proportion. On crystallization from chloroformether, there was obtained a colorless crystalline material corresponding to one of the diastereomers, Lactam C2 1.30 g., (26%) m.p. 148°-150° C. (Average yield in several preparations ranged from 26-30%).

ir (Nujol) 3400, 1750, 1725, 1650 cm⁻¹.

NMR (CDCl₃): 1.30 (d.3H), 1.95 (S.3H), 3.53 (S.3H), 2.85 (S.1H), 4.40 (two, q, overlaped, 2H) 4.55 (d, 2H), 5.10 (dd, 1H, J=5 Hz J=0 Hz). 5.30 (S,2H), 6.15 (dd,1H, J=0 Hz, J'=16 Hz), 6.80, (d, 1H, J=16 Hz) 7.2 7.45 (m5H), 7.60 (d, 2H, J=9 Hz), 8.20 (d, 2H, J=9 Hz), 9.15 (d, 1H, J=9 Hz).

CIMS. found M+1=524 (Calcd. MW=523).

Either the crystalline diastereomer C2 or the mixture of the two diastereomers could be used in the reactions described in Examples 3 and 4.

When the imine B1 used in the above experiment was derived from d-threonine, the Lactam C2 produced was noncrystalline and consisted of a mixture of two diastereomers in about equal amounts which could be separated by thin layer chromatography.

Using the same reaction conditions given in Example 2 the following β-lactams were also prepared:

1-(1'p-nitrobenzyloxycarbonyl-2'-hydroxy) propyl-3-(1''-methyl-2''-methoxycarbonyl) vinylamino-4-furyl-cis-3,4-azetidin-2-one Lactam C21

This compound was prepared in 65% yield from the potassium salt of (1-methyl-3-methoxycarbonyl) vinylamino acetic acid and the Schiff base derived from furfurylaldehyde and p-nitrobenzyl ester of dl-threonine. Recrystallization of the crude β-lactam afforded one of the two possible cis isomers with the following properties:

m.p. 147°-148°; (ir(Nujol); 3400, 1775, 1750, 1700, 1650 cm⁻¹; NMR (CDCl₃)δ: 1.40 (d,3H), 1.85 (s,3H), 3.60 (s,3H), 3.90 (s,1H, 4.55 (d,m,2H), 5.50 (d,1H, J=5 Hz), 5.20 (dd, 2H, J=5 Hz, J=9 Hz), 5.32 (s, 3H), 6.50 (m, 2H), 7.52 (d,1H), 7.55 (d, 2H, J=9 Hz), 8.25 (d, 2H, J=9 Hz), 8.9 (d, 1H J=9 Hz); CIMS: found M+1=488 (calc. MW=487).

1-(1'-p-nitrobenzyloxy carbonyl-2'-hydroxy) propyl-3-(1''-methyl-2''-methoxycarbonyl) vinylamino-4-o-nitrostyryl-cis-3,4-azetidin-2-one (Lactam C22)

The β-lactam was prepared in 25% yield from the Schiff base derived from o-nitrocinnamaldehyde and dl-threonine ester Crystallization of the crude product afforded a single diastereoisomeric compound mp 96°-99° C.

ir (Nujol): 3400, 1775, 1750, 1700 cm⁻¹; NMR (CDCl₃) δ: 12.30 (d, 3H), 1.90 (s,3H), 3.60 (s,3H) 3.70 (d, 1H), 4.10 (d,1H), 4.60 (m, 3H), 5.10 (dd, 1H, J=5), 5.25 (s, 2H), 6.15 (dd, 1H), 7.19 (d, 1H), 7.50 (m, 7H), 8.10 (d, 3HO, 8.18 (d, 1H, J=9 Hz).

(1''-methyl-2''-methoxy carbonyl) vinylamino-4-styryl-cis-3,4-azetidin-2-one (Lactam C23)

The β-lactam was prepared in 60% yield as an oil from the Schiff base derived from cinnamaldehyde and dl-phenyl serine p-nitrobenzyl ester. NMR spectrum of the crude material showed that the two diastereoisomeric β-lactams were formed in 20:80 ratio.

EXAMPLE 3

1-(1'-p-nitrobenzyloxycarbonyl-2'-hydroxy)propyl-3-phenoxyacetamido-4-styryl-cis-3,4-azetidin-2-one (Lactam E3)

To a suspension of Lactam C2 of Example 2 (3.98 g, 0.0076 mole) in 20 ml of dry acetone was added 1.44 g. (0.0076 mole) of p-toluenesulphonic acid monohydrate at room temperature. The reaction mixture was stirred for 1 hour when the p-toluenesulphonic acid salt of (IV) separated as a solid. Ether was added to the mixture which was cooled and filtered to obtain pure Lactam D' as a salt.

Lactam D' salt was suspended in 50 ml of dry methylene chloride to which was added 0.9 ml (0.0076 mole) of triethylamine. After stirring for 1 hour the reaction mixture was washed with water twice and dried ($Na_2SO_4$) and evaporated to provide Lactam D' as the free amine. It was dissolved in 50 ml of dry methylene chloride, and to this solution was added 0.9 ml (0.0076 mole) of triethylamine at $-10°$ C. Phenoxyacetyl chloride (1.124 g, 0.0076 mole) in 10 ml of methylene chloride was then added dropwise and the reaction mixture stirred for ½ hour at $-10°$ and then warmed up to room temperature in another 2 hours, evaporated to dryness under reduced pressure. The residue in chloroform was washed once with 3% sodium carbonate solution, water and dried ($Na_2SO_4$). Evaporation of the solvent followed by crystallization (chloroform-pet ether) gave white crystalline Lactam E3 3.36 g. (82%), which on recrystallization (chloroform-petroleum ether) gave 3.8 g. (72%) of pure Lactam E3 m.p. 130°-132° C.

ir (Nujol) 3400, 1750, 1740, 1700 cm$^{-1}$.

NMR (CDCl$_3$) 1.45 (d.3H), 3.9(S.1H), 4.45 (S.2H), 4.55 (2q. overlap J=not seen) 5.3 (q., J=not seen) 6.10 (dd, 1H, J=0 Hz, J=16 Hz), 6.6 7.3 (m,7H), 7.55 (d,2H, J=9 Hz), 825, (d, 2H J=9 Hz).

CIMS. Calc. for $C_{30}H_{29}N_3O_8$: 559, found: 560$_{(M+1)}$.

Lactam E3 produced from d-threonine-derived Lactam C2 was found to be a mixture of two diastereomers that could be separated by thin layer chromatography or column chromatography. One of these diastereomers was tested by $^1$H NMR spectrometry using a chiral europium shift reagent and found to be 100% optically pure.

EXAMPLE 4

1-(1'-p-nitrobenzyloxycarbonyl-2'-hydroxy)-prop-1'-enyl-3-phenoxyacetamido-4-styryl-cis-3,4-azetidin-2-one (Styryl Enol F 4)

Lactam E3 of Example 3 (9.84 g. 17 mmol.) was dissolved in 460 ml of dry acetone. To this solution was then added (in dropwise fashion) 8.89 ml of Jones reagent (2.67 mmoles of $H_2CrO_4$) while maintaining vigorous stirring. After two hours the reaction mixture was filtered through a coarse sintered glass funnel, concentrated "in vacuo" and the residual oil taken up in ethyl acetate. This solution was washed with (3×250 ml) of 5% $NaHCO_3$ aqueous solution dried ($Na_2SO_4$) and evaporated to yield Styryl Alcohol F4. It was crystallized from ethyl acetate, petroleum ether to give 4.00 g. of pure product (44%), mp 125°-127°.

ir 1740, 1670, 1630 cm$^{-1}$

NMR (CDCl$_3$) 2.25 (s,3H) 4.25 (s, 2H), 4.62 (dd, 1H, J=5 Hz, J'=9 Hz), 5.32 (dd, 1H, hidden) 5.35 (s,2H), 6.15 (dd, 1H, J=7 Hz, J'=16 Hz), 6.50 (d, 1H, J=16 Hz), 6.75 7.45 (m, 11H), 7.52 (d, 2H, J=8 Hz), 8.25 (d, 2H, J=8 Hz), NH hidden in (6.75 to 7.45), 13.00 (s, broad, 1H).

CIMS. calc. for $C_{30}H_{37}N_3O_8$: 557, found: 558 (M+1).

The same styryl Enol F4 was obtained when the reaction described in Examples 3 and 4 was carried out on the dl-diastereomeric mixture from reactions in Example 2.

EXAMPLE 5

1-(1'p-nitrobenzyloxycarbonyl-2'-mesyl)-prop-1'-enyl-3-phenoxyacetamido-4-styryl-cis-3,4-azetidin-2-one (Styryl Compound II5)

To a solution of 1.00 g. (7.8 mole) of Styryl Alcohol F4, Example 4, in 25 ml of dry dichloromethane was added 0.439 g (0.0036 mole) of N-N-dimethylaminopyridine (DMAP) in 10 ml of dichloromethane. A solution of 0.302 g (2.7 m mole) of mesyl chloride in 10 ml of dichloromethane was added all at once and the reaction mixture was stirred for 5 minutes. A thin layer chromatograph of the reaction mixture after 5 minutes showed the disappearance of the starting material. The organic layer was washed with 3 percent hydrochloric acid (3×20 ml), once with brine, and dried ($Na_2SO_4$). Evaporation of the solvent afforded an amorphous powder which was redissolved in ethyl acetate, dichloromethane (1:1), filtered through silica gel (10 g) and evaporated to yield 0.85 g of Styryl Compound II5.

ir (film) 3200, 2900, 1758, 1735, 1675, 1520 cm$^{-1}$.

NMR (CDCl$_3$): 2.25 (s, 3H), 3.30 (s, 3H), 4.40 (s, 2H), 4.75 (dd, 1H J=5 Hz), 5.25 (s, 2H), 5.45 (dd, hidden), 6.20 (dd, 2H, J=7 Hz), 6.80 (d, 1H, J=9 Hz), 6.10 7.30 (m, 11H), 7.50 (d, J=8 Hz), 8.20 (d, 2H, J=8 Hz).

EXAMPLE 6

1-(1'-p-nitrobenzyloxy-carbonyl-2'-mesyl) prop-1'-enyl-3-phenoxyacetamido-4-formyl-cis-3,4-azetidin-2-one (Aldehyde III6)

A solution of Styryl Compound II 5 of Example 5, 0.635 g (1 mmole) in 60 ml of anhydrous methylene chloride was cooled to $-78°$ C. A stream of ozone was passed through this solution for 5 minutes or until the solution turned blue. Oxygen was then flushed through the system for about one minute. Dimethyl sulfide 1 ml was added at $-78°$ C. and the solution was allowed to warm up to room temperature. The solution was washed once with brine (30 ml), then dried with $Na_2SO_4$ and evaporated to yield a crude oil, which on thin layer chromatography (CHCl$_3$,EtOAc at 1:1) showed two new spots at Rf about 0.9 (benzaldehyde) and Rf about 0.2 (the desired aldehyde). The same procedure was followed three more times (same scale each time). The combined work up resulted in 2.81 grams of crude oil which upon extraction with ether gave Aldehyde III 6 as a solid amorphous material 1.94 g. (69%), m.p. 148°-150° C.

ir (Nujol), 1780, 1765 cm$^{-1}$.

NMR (CDCl$_3$, DMSOd$_6$) 2.50(s, 3h), 3.45(s, 3H), 4.50(scdd, 3H), 5.30(s, and unseen doublet 3H), 6.70 to 7.40 (m, 5H), 7.60(d, 2h), 8.20(d, 3h), 8.95(d, 1H, 9.70(d, 1H J=1-2 Hz).

CIMS Calculation for $C_{24}H_{23}N_3O_{11}S$: 561, found 562 (M+1).

EXAMPLE 7

1-(1'-p-nitrobenzyloxycarbonyl-2'-mesyloxy) prop-1'-enyl-3-phenoxyacetamido-4-hydroxymethyl-cis-3,4-azetidin-2-one (Alcohol IV7)

Aldehyde III 6 of Example 6 (0.561 g, 1 mmole) was dissolved in 5.6 ml of anhydrous tetrahydrofuran under a nitrogen atmosphere. To the stirred solution at dry ice temperature was added 4 equivalents of 1 M diborane in tetrahydrofuran. The solution was warmed to room temperature and stirred for 8 hours after which time it was diluted with brine (10 ml) and 25 ml of $CH_2Cl_2$. The combined organic extracts were dried ($Na_2SO_4$) and evaporated to a crude oil, column chromatography of the oil gave 0.251 g of alcohol IV7 (48%).

NMR ($CDCl_3$), 2.50(s, 3H), 3.25(s, 3H), 5.30(M, 3H), 4.20(dd, 1H, J=5 Hz), 4.50(s, 2H), 5.60(dd, 1H, J=5 Hz, J'=9 Hz), 6.80 7.25(m, 5H), 7.50(d, 2H), 8.00(dd, not seen, 1H).

EXAMPLE 8

1-(1'-p-nitrobenzyloxycarbonyl-2'-mesyloxy) prop-1'-enyl-3-phenoxyacetamido-4-mesyloxymethyl-cis-3,4-azetidin-2-one (Ester V8)

To a solution of Alcohol IV of Example 7 (137 mg., 0.25 mmol) in methylene chloride (3 ml.) was added methanesulfonic anhydride (354 ml, 2.03 mmoles) in methylene chloride (3 ml). After stirring for 50 hours, the reaction solution was washed with brine (3 ml), dried ($Na_2SO_4$) and the organic solvent is evaporated to yield crude Ester V8.

1-(1'-p-nitrobenzyloxycarbonyl-2'-mesyloxy) prop-1'-enyl-3-phenoxyacetamido-4-chloromethyl-cis-3,4-azetidin-2-one (Ester V81)

To a solution of the alcohol IV of Example 7 (137 mg., 0.25 m mol.) in dimethylformamide is added excess of triphenyl phosphine and carbon tetrachloride under nitrogen atmosphere at −78°. After the usual work-up, the crude chloro derivative is obtained which can be used in place of ester V8 in the reactions described in Examples 9 and 10.

EXAMPLE 9 cis-3-methyl-4-(p-nitrobenzyloxycarbonyl)-7-phenoxyacetamido-$\Delta^3$-isocepham (isocephalosporin I9)

Through a cooled (0°) solution of Ester V8 of Example 8 (60 mg., 0.01 m mol) and methylene chloride (3 ml.) containing triethylamine (123 mg., 1.2 m mole) is bubbled hydrogen sulfide for 15 minutes. The flow of gas is then stopped and the reaction solution washed with brine (5 ml.), dried ($Na_2SO_4$) and the organic solvent is evaporated to yield Isocephalosporin I9.

Isocephalosporin I9 (40 mg., 0.0828 m mol) is dissolved in 1.2 ml. dioxane and methanol (0.6 ml.) containing 10% Pd-C (20 mg.) and hydrogenated at room temperature and at 50 psi for 3 hours. After filtering off the catalyst the solution is washed with aqueous $NaHCO_3$ brine and ethyl acetate. It is then acidified to pH 2 with dil HCl, extracted with ethyl acetate, dried ($Na_2SO_4$) and evaporated to yield the carboxylic acid of isocephalosporin I9 above.

EXAMPLE 10 cis-3-methyl-4(p-nitrobenzyloxycarbonyl)-7-phenoxyacetamido-$\Delta^3$oxa-2-isocepham (2-oxa isocephalosporin I10)

Procedure A

The dimesylate ester V8 of Example 8 (0.01 m mole), potassium acetate (0.04 m mole), dimethylformamide (5 ml) and water (0.1 ml) were stirred at room temperature for 20 hours. The resulting solution was mixed with 10 ml. ether, washed with water, dried ($Na_2SO_4$) and evaporated under reduced pressure. The above titled oily product was purified using preparative thin layer chromatography.

The oxa-2-isocepham I10 was converted to the corresponding 4-carboxy derivative mp 171°–172° (61%) by hydrogenolysis as described under Example 9.

Procedure B

The dimesylate ester V8 of Example 8 (0.488 m mole) is dissolved in anhydrous methylene chloride (12 ml.) and morpholine (1 m mol.) is added and the mixture stirred for 2 hours at room temperature. After evaporating methylene chloride the residue is redissolved in 12 ml of dioxane and stirred with p-toluene sulfonic acid monohydrate (1 m mol) for 3 hours. Dioxane is then evaporated and the residue redissolved in methylene chloride. This solution is washed with brine (15 ml.), dried ($Na_2SO_4$) and evaporated to yield the oily enol, cis-1-(1-p-nitrobenzyloxycarbonyl-2'-hydroxypropenyl)-3-phenoxy acetamido-4-mesyloxymethyl-2-azetidinone. Without further purification this enol is dissolved in anhydrous methylene chloride and triethylamine (0.57 m mol.) is added. The solution is refluxed for 2 hours, cooled, washed with brine, dried ($Na_2SO_4$) and evaporated to yield the above titled crude 2-oxaisocephalosporin I10. It is purified by preparative thin layer chromatography.

I claim:

1. A racemic or enantiomeric cis-3,4-azetidinone of formula VI or an unequal mixture of enantiomers thereof

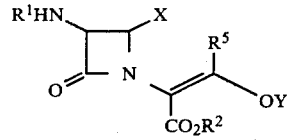

wherein $R^1$ is an N-acyl side chain of the $\alpha$-amino-$\beta$-lactam antibiotics which is selected from the group consisting of $R^3CO$ or alpha-alkyl-$\beta$-(alkoxycarbonyl)-vinyl, alpha-alkyl-beta-(alkylcarboxyl) vinyl, alpha-alkyl-beta-(alkyl)-beta-(alkoxycarbonyl) vinyl, alpha-alkyl-beta-(alkyl)-beta-(alkylcarbonyl)vinyl wherein each alkyl or alkoxy substituent of each said vinyl independently is from 1 to 3 carbons in length; $R^3$ being selected from (2-thienyl) methyl, (2-thienyl) methoxy, phenyl, benzyl, phenoxy, phenoxymethyl, phenylethyl, phenoxyethyl, the monosubstituted froms of said phenyl containing groups wherein the substituent is halogen, amino, carboxyl, carboxyester of 2 to 7 carbons, carboxamido, N-alkylcarboxamido of 1 to 4 carbons in the alkyl group PhCHNH₂, —CH₂NH₂, CH₃CHNH₂, HSCH₂CHNH₂,
|                          |              |

HOC₆H₅CH₂CHNH₂, PhCH₂CHNH₂, or HO₂C(CH₂)₂ CHNH₂;
         |                  |                        |

$R^2$ is hydrogen, benzyl, p-nitrobenzyl, phenyl, p-biphenyl or alkyl of 1 to 3 carbon atoms;

$R^5$ is hydrogen, alkyl of 1 to 3 carbons, phenyl, furyl, thienyl, acetoxymethyl or S-(N-methyltetrazol-1-yl) thiomethyl;

X is hydroxy, methanesulfonoxy, p-toluenesulfonoxy, trifluoromethanesulfonoxy, alkylcarbonato of 2 to 4 carbons, benzylcarbonato, chloro, bromo or iodo, and;

Y is methanesulfonyl, p-toluenesulfonyl, trifluoromethanesulfonyl, alkoxycarbonyl of 2 to 4 carbons or benzyloxycarbonyl.

2. An azetidinone according to claim 1 wherein $R^2$ is p-nitrobenzyl.

3. An azetidinone according to claim 1 wherein X is hydroxy.

4. An azetidinone according to claim 1 wherein X is methanesulfonoxy and Y is methanesulfonyl.

5. The azetidinone according to claim 1 wherein $R^1$ is phenoxyacetyl, $R^2$ is p-nitrobenzyl, $R^5$ is methyl, X is hydroxy and Y is methanesulfonyl.

6. The azetidinone according to claim 1 wherein $R^1$ is phenoxyacetyl, $R^2$ is p-nitrobenzyl, $R^5$ is methyl, X is methanesulfonoxy and Y is methanesulfonyl.

* * * * *

UNITED STATES PATENT AND TRADEMARK OFFICE
CERTIFICATE OF CORRECTION

PATENT NO. : 4,440,682
DATED : April 3, 1984
INVENTOR(S) : Bose, Fernandez & Gala It is certified that error appears in the above—identified patent and that said Letters Patent is hereby corrected as shown below:

Column 10, Line 51 change "41.38" to --41.83--

Column 13, line 37, change "6.67.3" to --6.6 7.3--.

Signed and Sealed this

Eleventh Day of December 1984

[SEAL]

Attest:

GERALD J. MOSSINGHOFF

Attesting Officer

Commissioner of Patents and Trademarks